United States Patent [19]
Safe

[11] Patent Number: 6,136,845
[45] Date of Patent: Oct. 24, 2000

[54] ENDOCRINE THERAPY FOR BREAST CANCER: COMBINED TREATMENT WITH TAMOXIFEN PLUS ALKYL PCDFS

[75] Inventor: Stephen H. Safe, College Station, Tex.

[73] Assignee: The Texas A&M University System, College Station, Tex.

[21] Appl. No.: 09/217,780

[22] Filed: Dec. 21, 1998

[51] Int. Cl.⁷ .......................... A61K 31/38; A61K 31/135
[52] U.S. Cl. .............................................. 514/443; 514/648
[58] Field of Search ...................................... 514/443, 648

[56] References Cited

U.S. PATENT DOCUMENTS

| 4,656,187 | 4/1987 | Black et al. | 514/648 |
| 5,516,790 | 5/1996 | Safe | 514/443 |
| 5,604,248 | 2/1997 | Bryant et al. | 514/648 |

*Primary Examiner*—Jerome D. Goldberg
*Attorney, Agent, or Firm*—Fulbright & Jaworski, L.L.P.

[57] ABSTRACT

Methods and pharmaceutical combinations for inhibiting estrogen-dependent tumors via the co-administration of anti-estrogen triphenylethylenes, including tamoxifen, and alkyl PCDFs.

19 Claims, 3 Drawing Sheets

ENDOCRINE THERAPY FOR BREAST CANCER: COMBINED TREATMENT WITH TAMOXIFEN PLUS ALKYL PCDFS

FIELD OF THE INVENTION

This invention relates to tumor therapy and prevention. More particularly, it relates to methods and pharmaceutical combinations for inhibiting estrogen-dependent tumors.

BACKGROUND OF THE INVENTION

Many breast tumors are estrogen-dependent, meaning that they require estrogens for growth. For several years, a popular and successful breast tumor treatment strategy has employed antiestrogens. Antiestrogens (such as tamoxifen) are a class of compounds which inhibit estrogens from eliciting their full response in target tissues. Tamoxifen has also been used as a prophylatic drug for women with a high risk for breast cancer. However, many antiestrogens do not act as strict antagonists, but rather also act as partial agonists on the estrogen receptor (ER). This partial agonist activity has proven to be a 'double-edged sword'. While the partial agonist activity has been shown to produce beneficial effects such as reducing serum cholesterol and preventing osteoporosis, it has recently been implicated by a number of independent studies as promoting increased endometrial tumor formation. (Endometrial cells consist of stromal and luminal epithelial cells, which in addition to smooth muscle myometrial cells, comprise the major cell types of the uterus.) For instance, findings from the National Surgical Adjuvant Breast and Bowel Project concluded that "Risk of endometrial cancer increases following tamoxifen treatment for breast cancer; however, net benefit greatly outweighs risk" (Fisher et al. (1994)). The increased incidence of endometrial cancer after adjuvant tamoxifen therapy for breast cancer was recently confirmed in a study of 87,323 women with breast cancer as well as others (Rutqvist et al. (1995), Fornander et al. (1989), Mouridsen et al. (1988), Ryden et al. (1986)). The partial agonistic or "estrogen-like" activity of tamoxifen in the human uterus and the effects of tamoxifen on increased incidence of endometrial cancer is consistent with previous studies in laboratory animal and cell culture models. For instance, tamoxifen induced uterine hyperplasia in most animal models and tumor growth in athymic nude mice bearing transplanted estrogen-responsive endometrial tumors.

Thus, the prior art method treating estrogen-dependent breast tumors results in a significant increase in the incidence of endometrial tumors. This increased incidence of endometrial tumors may be due to estrogen-like activity of tamoxifen in the uterus.

More recently, another area of research has focused on the antiestrongenic activity of aryl hydrocarbon receptor (AhR) agonists using 2,3,7,8-tetrachlorodibenzo-p-dioxin (TCDD) as a model compound. TCDD and related compounds inhibit mammary tumor growth in rodent models and 17β-estradiol (E2)-induced responses in the rodent uterus and human breast cancer cells. While TCDD was demonstrated to be an effective antiestrogen in rats, mice, and MCF-7 human breast cancer cell lines in culture, it proved to be too hepatocarcinogenic for use as a therapeutic antiestrogenic. Previous studies have demonstrated that TCDD induces toxic and biochemical responses in the rat; one such biochemical response, instruction of CYP1A1 dependent aryl (hydrocarbon hydroxylase (AHH) or ethoxyresorufin O-deethylase (EROD) activities in the liver correlates with the toxicity of TCDD.

A series of 6-alkyl-1,3,8-trichlorodibenzofurans (triCDFs) were originally synthesized for investigating their activities as partial AhR antagonists. The 6-alkyl-1,3,8-triCDFs are of the formula:

where $R_1$, $R_3$, and $R_8$ are chlorine, $R_6$ is a linear of branched alkyl group of one to four carbons, and $R_2$, $R_4$, $R_7$, and $R_9$ are hydrogen. 6-methyl-1,3,8-trichlorodibenzofuran (6-MCDF) was used as a prototype for this series of compounds.

Initial studies showed that 6-MCDF bound to the Ah receptor but was a weak inducer of CYP1A1 and exhibited minimal toxicity. Moreover, 6-MCDF inhibiter TCDD induced toxic responses and was characterized as an Ah receptor antagonist, (B. Astroff et al. (1988); M. Harris et al. (1989); R. Bannister et al. (1989); C. Yao et al. (1989)). However, 6-MCDF did not inhibit TCDD-induced antiestrogenic activity; 6-MCDF was also an antiestrogen in the rat uterus. (B. Astroff and Safe (1991)). In 1988, Astroff and Safe reported that both TCDD and 6-MCDF caused a dose-dependent decrease in nuclear and cytosolic ER and progesterone receptor (PR) binding in 21 to 25 day-old female Sprague-Dawley rat uterus. Moreover, 6-MCDF was only 300 to 570 times less active than TCDD as an antiestrogen while it was >157,000 times less potent than TCDD as an inducer of hepatic CYP1A1 in the same animals (CYP1A1 is a surrogate for toxic potency). Subsequent studies showed that 6-MCDF and related compounds inhibited E2-indued hypertrophy, peroxidase activity, cytosolic ER and PR binding, and EGF receptor and c-fos mRNA levels in the rat uterus. Thus, it was apparent that 6-MCDF was capable of the beneficial antiestrogenicity effect without the toxic side effects of TCDD.

The in vivo antiestrogenic activity of a series of alkyl-substituted polychlorinated dibenzofurans (PCDFs) has been investigated in the immature female Sprague-Dawley rat uterus (B. Astroff et al. (1991); R. Dickerson et al. (1995)). The compounds utilized in this study contain two, three, or four lateral substituents and include: 6-MCDF, 6-ethyl-1,3,8-triCDF, 6-n-propyl-1,3,8-triCDF, 6-i-propyl-1,3,8-triCDF, 6-t-butyl-1,3,8-triCDF, 8-MCDF (two lateral substituents); 6-methyl-2,3,8-triCDF, 6-methyl-2,3,4,8-tetraCDF, 8-methyl-1,3,7-triCDF, and 8-methyl-1,2,4,7-tetraCDF (three lateral substituents); 8-methyl-2,3,7-triCDF, 8-methyl-2,3,4,7-tetraCDF (four lateral substituents). Two additional compounds, 8-methyl-2,3,7-trichlorodibenzo-p-dioxin and 8-methyl-2,3,7,-tribromodibenzo-p-dioxin (four lateral substituents), were also investigated. All alkyl-substituted compounds inhibited estrogen-induced uterine wet weight increase and cytosolic and nuclear PR and ER binding. Quantitative structure-antiestrogenicity relationships were determined using 6-i-propyl-1,3,8-triCDF, 6-methyl-2,3,4,8-tetraCDF, and 8-methyl-2,3,4,7-tetraCDF as representative congeners containing two, three and four lateral substituents, respectively. The $ED_{50}$ values ($ED_{50}$ is defined as the dose which produces 50% of a maximal response) for antiestrogenicity were similar for the three compounds; however the $ED_{50}$ values for induction of hepatic CYP1A1-dependent activity were 73,600 (estimated), 8.52, and 5.31 mmol/kg for 6-i-propyl-1,3,8,-triCDF, 6-methyl-2,3,4,8-tetraCDF, and 8-methyl-2,3,4,7-tetraCDF, respectively. Based on results of previous studies, CYP1A1 can be used as a surrogate for toxic potency in the rat; therefore, high $ED_{50}$(CYP1A1 induction)/$ED_{50}$ (antiestrogenicity) ratios are indicative of low toxicity and high antiestrogenic potency. The ratio was 13,990–17,100 for 6-i-propyl-1,3,8-triCDF, whereas corresponding ratios for the compounds with three and four lateral substituents varied from 0.64–3.34. These data suggested that alternate 1,3,6,8-substituted alkyl PCDFs are useful structural models for developing new AhR-mediated antiestrogens for treatment of breast cancer. Data regarding the antiestrogenic effects of 1,3,6,8- or 2,4,6,8-alternate substituted alkyl dibenzofurans have been presented in U.S. Pat. No. 5,516,790 and are hereby incorporated by reference in their entirety.

The in vivo antitumorigenic activity of 6-MCDF, 8-MCDF (8-methyl-1,3,6-triCDF) and 6-cyclohexyl-1,3,8-triCDF (6-CHDF) were investigated in the DMBA rat mammary tumor model (McDougal et al., Inhibition of 7,12-dimethylbenz[a]anthracene-induced rat mammary tumor growth by aryl hydrocarbon receptor agonists. *Cancer Letters* 120:53–63, 1997. At doses of 5, 10 or 25 mg/kg/wk, 6- and 8-MCDF significantly inhibited mammary tumor growth, and at the 5 mg/kg/wk dose, >50% growth inhibition was observed for both isomers. In contrast, 6-CHDF was inactive at the 5 mg/kg/wk dose, and the structure-antitumorigenicity relationships (6-/8-MCDF>>6-CHDF) correlated with structure-antiestrogenicity (rat uterus) studies and the relative binding affinities of these compounds for the AhR. The antitumorigenic activity of 6- or 8-MCDF in the mammary was not accompanied by any significant changes in liver/body weight ratios, liver morphology or induction of hepatic CYP1A1-dependent activity which is one of the most sensitive indicators of exposure to AhR agonists. RT-PCR and Western blot analysis of mammary tumor mRNA and protein extracts, respectively, confirmed the presence of the AhR suggesting that AhR-mediated signaling pathways are functional in rat mammary tumors, but simply not activated by 6- or 8-MCDF.

This invention is based on utilizing a well-described antiestrogenic drug (tamoxifen) in combination with alkyl PCDF's. The alkyl PCDFs can interact with tamoxifen (actively) and in combined treatment over the effective dose of tamoxifen required for treatment of breast cancer and at the same time provide protection from tamoxifen-induced endometrial cancer.

While not intending to be bound by theory, it is believed that tamoxifen and alkyl PCDFs function via two different mechanisms. AhR is believed to decrease the ER by an unknown mechanism (presumably posttranscriptional). It is believed that alkyl PCDFs work through the AhR which cross-talks with the ER. Tamoxifen is believed to bind the ER and block ER action in the breast. 6-MCDF is believed to act through the AhR and therefore bind to the receptor. 6-MCDF is believed to be an AhR antagonist for the toxic responses (i.e., it inhibits TCDD toxicity in co-treatment studies) but is believed to act as an Ah receptor agonist for antiestrogenicity (i.e., acts like TCDD).

The prior art method of treating estrogen-dependent breast tumors frequently involves the administration of tamoxifen. As mentioned above, tamoxifen therapy has been shown to be associated with a significantly elevated incidence for endometrial tumor formation in several independent trials (Fomander et al. (1989), Rutqvist et al. (1995), Mouridsen et al. (1988), Ryden et al. (1986), Fisher et al. (1994)). Some studies have suggested that the incidence of endometrial tumor formation may be reduced with lower tamoxifen doses. The Stockholm trial demonstrated an approximately 6 fold higher risk for endometrial tumors with a treatment protocol of 40 mg/day for 2 years (Fomander et al. (1989), Rutqvist et al. (1995)), while the Danish and South-Swedish trials demonstrated only 3.3 and 2.0 fold higher risks, respectively. In the latter two trials, tamoxifen was administered at 30 mg/day for one year. In Scottish and Manchester England trials in which tamoxifen was administered at 20 mg/day, there appeared to be no increased risk for endometrial tumors (Stewart et al. (1989), Stewart (1992), Ribeiro et al. (1992)). However, a third study involving 2843 patients demonstrated a 7.5 fold increased risk for endometrial tumor formation with the same dose (20 mg/day) of tamoxifen (Fisher et al. (1994)). In light of the smaller population sizes of the former studies, the results of the Scottish and Manchester England trials should be interpreted cautiously. Thus, it appears clear from the preponderance of studies that tamoxifen therapy results in significantly increased risks for endometrial tumor formation. However, it is presently unclear from existing trials whether a reduction in tamoxifen dose results in a reduced risk of endometrial tumor formation.

Although there is no clear indication that reducing tamoxifen dose correspondingly reduces the risk for endometrial tumor formation, it should be kept in mind that large population based trials have not been conducted with tamoxifen doses less than 20 mg/day. Data from animal and cell culture models, however, do suggest a dose-related uterotropic effect for tamoxifen and this is consistent with pharmacological principles. For example, tamoxifen produced significant dose dependent increases in rat uterine wet weight which correlated with increased drug concentration. Therefore, it follows that similar reductions in tamoxifen dose might also result in diminished endometrial tumor formation.

What is needed is a method for reducing the necessary concentration of tamoxifen without reducing efficacy. Ideally, such a method should maintain the beneficial effects of tamoxifen (such as on maintaining bone mass) and minimize the tumorogenic effects of tamoxifen in the uterus.

SUMMARY OF THE INVENTION

The present invention provides a formulation for the inhibition of estrogen-dependent tumors comprising a 1,3, 6,8-substituted or 2,4,6,8-substituted alkyl PCDF in combination with another compound which is tamoxifen or a related compound of the triphenylethylene class. The triphenylethylene class of compounds includes, but is not limited to tamoxifen, toremifene, and other triphenylethylene derivatives.

It will be understood that the present invention involves the administration and use of PCDFs in combination with antiestrogen triphenylethylene compounds. This group of antiestrogen triphenylethylene compounds includes, but is not limited to, tamoxifen, tamoxifen analogs and derivatives and toremifene, toremifene analogs and toremifene derivatives. This encompasses, but is not limited to, all such compounds, and equivalents thereto, which are, for example, disclosed in the following U.S. patents, each of which is hereby incorporated by reference herein in its entirety: U.S. Pat. No. 5,807,899, issued to Bohlmann et al., Sep. 15, 1998; U.S. Pat. No. 5,750,576, issued to DeGregorio on May 12, 1998; U.S. Pat. No. 4,656,187, issued to Black et al. on Apr. 7, 1987; U.S. Pat. No. 5,554,628, issued to Bryant et al. on Sep. 10, 1996; U.S. Pat. No. 5,604,248, issued to Bryant et al. on Feb. 18, 1997; and U.S. Pat. No. 5,691,355, issued to Bryant et al. on Nov. 25, 1997.

The term inhibition in this invention indicates either a reduction in the rate of tumor growth, tumor size, tumor volume, or even complete elimination of a tumor. Furthermore, it can indicate delaying onset of a tumor or complete prevention of tumor occurrence (for prophylatic treatment of high risk patients) or recurrence (following prior estrogen-dependent tumor treatment).

This invention further provides a method of treating a person or animal (hereinafter referred to as a patient) with an estrogen-dependent tumor with the above formulation comprising administering a biologically-active amount of the formulation. The above formulation can be administered such that both compounds are delivered at the same time or at different times.

This invention provides significant improvements to the prior art by providing a combination formulation of a triphenylethylene derivative and a 1,3,6,8-substituted or 2,4,6,8-substituted alkyl PCDF which act together, synergistically or additively, to inhibit estrogen-dependent tumor growth. The result of this combined effect is that the concentration at which the triphenylethylene derivatives are effective can be reduced, thus reducing the potential for endometrial tumor induction. Furthermore, in addition to the reduction of endocrine tumorogenicity due to the reduced concentration of triphenylethylene needed, the 1,3,6,8-substituted alkyl PCDF compounds act as direct inhibitors of tamoxifen-induced endometrial tumor formation. In addition, 1,3,6,8-substituted or 2,4,6,8-substituted alkyl PCDFs do not inhibit the beneficial actions of tamoxifen of maintaining bone density. Thus, the addition of a 1,3,6,8-substituted or 2,4,6,8-substituted alkyl PCDF allows for 1) a reduced, yet effective, concentration of a triphenylethylene derivative, 2) provides direct anti-endometrial tumor activity, and 3) does not reduce the beneficial effect of tamoxifen on maintaining bone density.

DETAILED DESCRIPTION OF THE PREFERRED EMBODIMENT

The present invention provides a formulation for the inhibition of estrogen-dependent tumors comprising a 1,3, 6,8-substituted or 2,4,6,8-substituted alkyl PCDF used in combination with a second compound of the triphenylethylene class. Possible substituents include halogens such as bromine, chlorine, fluorine and/or linear or branched substituents such as alkyl groups of about one to about five carbons. The 2,4,6 or 8 and 1,3,6 or 8 positions may also be individually and independently occupied by a hydrogen instead of a substituent. Suitable alkyl substituents include, but are not limited to, methyl, ethyl, propyl, isopropyl (i-propyl), n-butyl, sec-butyl, or tert-butyl groups.

The PCDFs used in the present invention are described, for example, in U.S. Pat. No. 5,516,790, issued to Stephen Safe on May 14, 1996, which is hereby incorporated by reference herein in its entirety. The PCDFs may include, but are not limited to, those having the formula:

wherein $R_1$, $R_3$, $R_6$ and $R_8$ or $R_2$, $R_4$, $R_6$ and $R_8$ are individually and independently a hydrogen or a substituent selected from the group consisting of chlorine, fluorine and bromine, and a linear or branched alkyl group of one to four carbons, and wherein the compound has at least one alkyl substituent and at least two halogen substituents; furthermore, the halogen may be chlorine, the alkyl substituent may be selected from the group consisting of methyl, ethyl and propyl; $R_6$ may be an alkyl substituent and $R_1$, $R_3$, and $R_8$ may be selected from the group consisting of chlorine, fluorine and bromine; further still $R_8$ may be an alkyl substituent and $R_1$, $R_3$, and $R_6$ may be selected from the group consisting of chlorine, fluorine and bromine, the alkly substituent may be methyl; still further $R_6$ may be an alkyl and $R_2$, $R_4$, and $R_8$ may be selected from the group consisting of chlorine, fluorine and bromine; and, for example, $R_8$ may be an alkyl substituent and $R_2$, $R_4$, and $R_6$ may be selected from the group consisting of chlorine, fluorine and bromine. Examples of PCDFs may include, but are not limited to, 6-methyl-1,3,8-trichlorodibenzofuran,
8-methyl-1,3,6-trichlorodibenzofuran,
6-ethyl-1,3,8-trichlorodibenzofuran, 6-propyl-1,3-8-trichlorodibenzofuran,
6-methyl-2,3,8-trichlorodibenzofuran,
6-methyl-2,3,4,8-tetrachlorodibenzofuran,
8-methyl-1,3,7-trichlorodibenzofuran,
8-methyl-1,2,4,7-tetrachlorodibenzofuran,
8-methyl-2,3,7-trichorodibenzofuran, and
8-methyl-2,3,7-tetrachlorodibenzofuran.

In one embodiment, PCDFs possessing two lateral substituents ('lateral' substituents may be on position 2,3,7, or 8 of dibenzofuran) is used in combination with tamoxifen. In a preferred embodiment, 6-MCDF is used as a representative PCDF in combination with tamoxifen. In another preferred embodiment, 6-i-propyl-1,3,8-triCDF is used in combination with tamoxifen. In yet another preferred embodiment, 8-MCDF is used as a representative PCDF in combination with tamoxifen. The PCDF and the triphenylethylene class compounds are combined in a ratio by weight essentially 50:1 to 1:50, preferably 25:1 to 1:25, and more preferably 10:1 to 1:10. Most preferred ratios for alkyl PCDF: tamoxifen are 1:1 to 1:4 to 4:1 (PCDF:Tamoxifen).

The present invention also provides a method for the treatment of estrogen-dependent tumors comprising administering to a patient a therapeutically effective amount of a PCDF in combination with a triphenylethylene class compound (see above). The PCDF and the triphenylethylene class compounds are administered simultaneously or sequentially. Simultaneous administration of the compounds is the preferred method of delivery. In the event of sequential delivery, however, it is preferred that the first administered compound still be bioactive at the time that the second compound is delivered. In one embodiment, both the PCDF and the triphenylethylene class compounds are delivered orally. They may also, for example, be administered intraperotineally.

EXAMPLE 1

Female virgin Sprague-Dawley rats were obtained from Harlan (Houston) and were allowed to acclimate for 10 days, allowed access to food and water ad libitum, and maintained on a 12 h light/dark schedule. Mammary tumors were induced in 50±3 day old-rats by administering a single gavage dose of 20 mg DMBA in 0.5 ml corn oil. After 30 to 75 days, tumors could be detected by palpitation in the ductal tubes of the mammary glands. Multiple tumors often developed on a single rat. When the tumor or the largest of the tumors reached a small size (50–100 mm$^3$), rats were treated daily by gavage with corn oil alone (vehicle control), 0.4 mg/kg 6-MCDF, 0.4 mg/kg tamoxifen, or a cotreatment of 0.4 mg/kg 6-MCDF plus 0.4 mg/kg tamoxifen for 20 days, and then euthanized on the 21$^{st}$ day. Tumor sizes were measured with calipers, and volumes were calculated by formula (length×width×depth)/6π and are expressed as percent control. One week after their last injection, rats were euthanized by asphyxiation. All tumors were removed, weighed, and sectioned. One portion was frozen in liquid nitrogen for PCR analysis; one portion was placed in 10% formalin for histopathological analysis; and the majority was immediately homogenized for the preparation of microsomal and cytosolic fractions. Livers were perfused and weighed, and cytosol and microsomes were prepared as previously described.

The results of this study are summarized in Table 1. At doses of 0.4 mg/kg/day, both tamoxifen and 6-MCDF alone significantly inhibited tumor volume (58.5 and 66.4% inhibition, respectively).

TABLE 1

| | % Inhibition | |
|---|---|---|
| treatment | tumor volume | tumor weight |
| tamoxifen | 58.5* | NS decrease |
| 6-MCDF | 66.4* | NS decrease |
| tamoxifen/6-MCDF | 86.2* | 78.0* |

Percent inhibition of tumor volume or tumor weight with tamoxifen alone (0.4 mg/kg/day), 6-MCDF alone (0.4 mg/kg/day), and tamoxifen plus 6-MCDF (each 0.4 mg/kg/day).
*P < 0.05 compared to untreated control using ANOVA and Duncan's statistical test for significance.

Both drugs alone also decreased tumor weight; however, this inhibitory response was not significant. In contrast, there was a significant 86.2 and 78.0% inhibition of both mammary tumor volume and tumor weight in animals cotreated with tamoxifen plus 6-MCDF. The results illustrated in Table 1 clearly show that tumor growth in animals cotreated with both drugs is essentially blocked. Moreover, treatment with the compounds alone or in combination did not affect body or organ weights or cause any apparent histopathological changes in these tissues. The induction of CYP1A1-dependent EROD activity by toxic halogenated aromatics such as TCDD is one of the most sensitive indicators of exposure to these compounds and there is an excellent correlation between toxic versus EROD induction potencies. Alternate-substituted PCDFs are characterized by their low toxicity and low potency as inducers of hepatic EROD activity. The results summarized in Table 1 show that tamoxifen, 6-MCDF and tamoxifen plus 6-MCDF did not induce hapatic EROD activity and this is consistent with the low toxicity of 6-MCDF. These results clearly demonstrate that 6-MCDF enhances the antitumorigenic activity of tamoxifen in the DMBA-induced rat mammary tumor model indicating that combined treatment with tamoxifen plus alkyl PCDFs is a new and more effacious endocrine therapy for treatment of mammary cancer.

EXAMPLE 2

Figure 1:
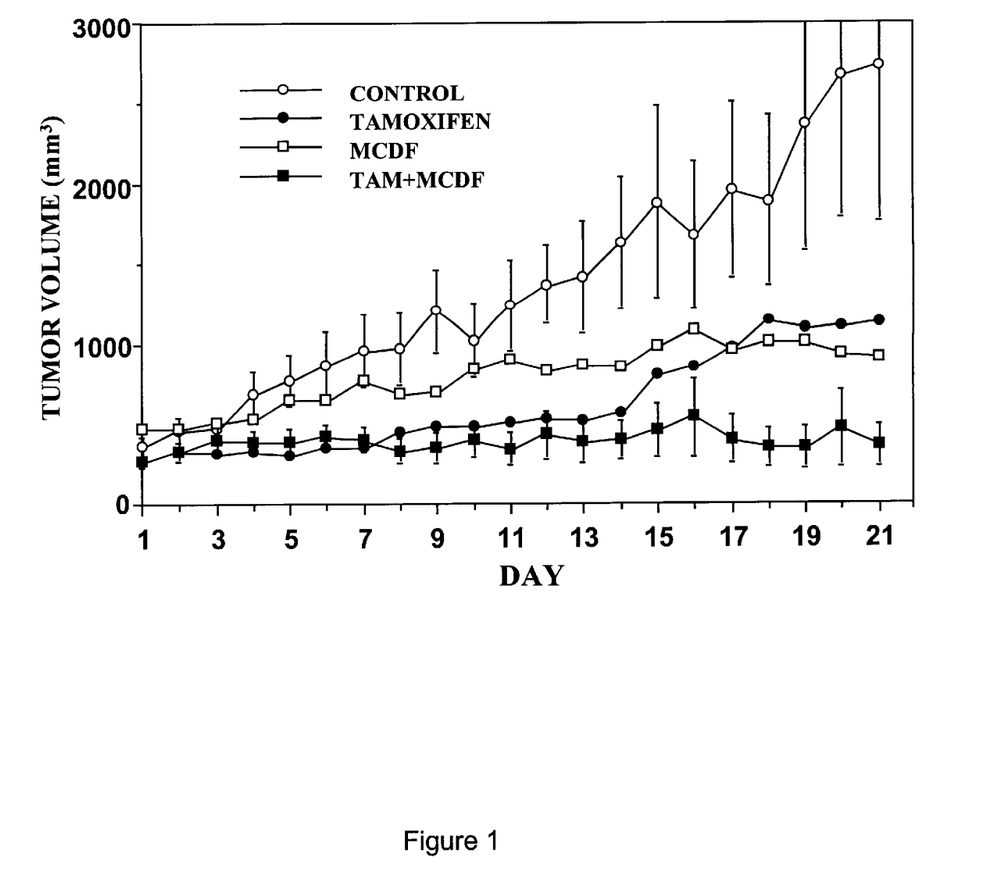
FIG. 1 shows tumor volume and the effect of treatment with tamoxifen, MCDF, or co-treatment.

Example 2, summarized in Table 2 and FIG. 1, shows the effects of 6-MCDF and Tamoxifen, alone and in combination in the DMBA-induced rat mammary tumor model.

Methods: Exact aged virgin female Sprague-Dawley rats were dosed on day 55 in the afternoon with 20 mg/rat 7,12-dimethylbenz[a]anthacene in a volume of 0.5 ml/rat corn oil (rats weigh approximately 165 g, resulting in 120 mg/kg DMBA and 3 ml/kg corn oil). Rats were treated by gavage daily with corn oil (vehicle), 0.4 mg/kg 6-MCDF, 0.4 mg/kg Tamoxifen, or a cotreatment of 0.4 mg/kg 6-MCDF plus 0.4 mg/kg Tamoxifen for 20 days, and then euthanized on the 21$^{st}$ day.

TABLE 2

EFFECTS OF 6-MCDF AND TAMOXIFEN, ALONE AND IN COMBINATION, IN THE DMBA-INDUCED RAT MAMMARY TUMOR MODEL

|  | CONTROL | TAMOXIFEN | 6-MCDF | TAM ± MCDF |
|---|---|---|---|---|
| Number of animals | 13 | 13 | 11 | 10 |
| Final Tumor Volume ($mm^3$) | 2734 ± 956 | 1135 ± 587* | 918 ± 305* | 376 ± 111** |
| Final Tumor Volume (% Control) | 100 ± 31.5 | 41.5 ± 20* | 33.6 ± 11.2* | 18.8 ± 4.1** |
| Tumor Weight (g) | 3.82 ± 1.18 | 2.35 ± 1.16 | 1.68 ± 0.53 | 0.84 ± 0.27* |
| Tumor Wt (% Control) | 100 ± 27.7 | 61.5 ± 30.4 | 43.9 ± 12.8 | 22.0 ± 6.3* |
| EROD activity (pmol/mg/min) | 118 ± 40 | 169 ± 74 | 140 ± 32 | 92 ± 21 |
| Final Body Weight (g) | 250 ± 5 | 243 ± 4 | 247 ± 4 | 244 ± 4 |
| Liver weight (% BW) | 3.13 ± 0.12 | 3.64 ± 0.18 | 3.49 ± 0.16 | 3.32 ± 0.19 |
| Uterine Wt. (% BW) | 0.212 ± 0.017 | 0.142 ± 0.006* | 0.230 ± 0.037 | 0.146 ± 0.10 |
| Heart weight (% BW) | 0.374 ± 0.005 | 0.420 ± 0.018 | 0.405 ± 0.10 | 0.395 ± 011 |
| Spleen Wt. (% BW) | 0.257 ± .022 | 0.236 ± 0.019 | 0.255 ± 0.017 | 0.213 ± 0.008 |
| Kidney weight (% BW) | 0.349 ± 0.007 | 0.386 ± 0.012 | 0.361 ± 0.016 | 0.397 ± 0.027 |

*$p < 0.05$
**$p < 0.01$
Statistical Analysis was done using ANOVA, and significance was determined using the Duncan New Multiple Range test.

FIG. 1 shows tumor volume and the effect of treatment on mammary tumors of 0.4 mg/kg/day tamoxifen, MCDF, or co-treatment.

EXAMPLE 3

Example 3 shows bone effects of daily doses of tamoxifen and 6-MCDF in ovariectomized rats. The ovariectomized rat is used as a model for osteoporosis. Current studies measure bone histomorphometry (Evans et al. (1996) or bone mineral density with X-ray abosrptiometry (Ezawa (1995) as well as bone length, wet weight and dry weight (Takahashi et al. (1996). In 1987 it was reported that tamoxifen acted as an estrogen agonist in bone tissue of ovariectomized rats (Turner et al. (1987), although a study indicates that tamoxifen has no effect in cycling rats (Takahashi et al. (1996). The femurs of rats treated with Tamoxifen, MCDF, or Tamoxifen+MCDF were analyzed to determine the tissue-specific antiestrogenicity of MCDF.

Methods: Rats were ovariectomized at 97 days of age. After approximately 3 weeks, rats were orally closed for 20 days with corn oil (vehicle), 0.4 mg/kg/day tamoxifen, 0.8 mg/kg/day 6-MCDF, or cotreatment of 0.4 mg/kg tamoxifen plus 0.8 mg/kg 6-MCDF daily. Rats were euthanized on day 21. After uteri were excised and processed, both left and right femurs were excised and the length measured with calipers. Because there was no cheap protocol in the literature for loosening all the muscle from the bone, a 4 hour wash with PBS, pH 2.0, was used, and softened the connective tissue without visibly affecting the bone. Wet weight was measured after residual connective tissue was stripped away. Dry weight was measured after the bones were dried for 12 ours at 130° C.

TABLE 3

BONE EFFECTS OF DAILY DOSES OF TAMOXIFEN (0.4 mg/kg) AND 6-MCDF (0.8 mg/kg) IN THE OVARIECTOMIZED SPRAGUE-DAWLEY RAT

|  | CONTROL | TAMOXIFEN | 6-MCDF | TAM + MCDF |
|---|---|---|---|---|
| Wet bone weight (% body weight) | 0.347 ± 0.009 | 0.403 ± 0.007* | 0.341 ± 0.008 | 0.412 ± 0.020* |
| Dry bone weight (% body weight) | 0.180 ± 0.005 | 0.216 ± 0.005* | 0.183 ± 0.003 | 0.235 ± 0.010* |

TABLE 3-continued

BONE EFFECTS OF DAILY DOSES OF
TAMOXIFEN (0.4 mg/kg) AND 6-MCDF (0.8 mg/kg)
IN THE OVARIECTOMIZED SPRAGUE-DAWLEY RAT

|  | CONTROL | TAMOXIFEN | 6-MCDF | TAM + MCDF |
|---|---|---|---|---|
| Bone length index (mm/body weight × 100) | 12.1 ± 0.4 | 14.2 ± 0.3* | 12.17 ± 0.3 | 15.0 ± 0.9* |

Values expressed as means ± standard errors.
*Significantly different ($p < 0.05$) from control treatment.

EXAMPLE 4

Example 4 shows uterine effects of daily doses of tamoxifen and 6-MCDF in ovariectomized rats.

Methods: Rats were ovariectomized at 97 days of age, and treatments began at 117 days of age. Rats were orally dosed for 20 days with corn oil (vehicle), 0.4 mg/kg/day tamoxifen, 0.4 mg/kg/day 6-MCDF, or a co-treatment of 0.4 mg/kg/day tamoxifen plus 0.4 mg/kg/day 6-MCDF, with 5 rats in each treatment group. Rats were euthanized on day 21. 6-MCDF caused a slight but significant increase in splenic wet weight.

TABLE 4

UTERINE EFFECTS OF DAILY DOSES OF
TAMOXIFEN (0.4 mg/kg) AND 6-MCDF (0.4 mg/kg)
IN THE OVARIECTOMIZED SPRAGUE-DAWLEY RATE

|  | CONTROL | TAMOXIFEN | MCDF | TAM + MCDF |
|---|---|---|---|---|
| Uterine Wet Weight (% body wt) | 0.045 ± 0.002 | 0.085 ± 0.004* | 0.060 ± 0.006 | 0.078 ± 0.004* |
| Uterine Wet Weight (g) | 0.131 ± 0.006 | 0.211 ± 0.011* | 0.180 ± 0.019* | 0.195 ± 0.012* |
| Uterine Peroxidase Assay (Abs/mg protein) (Fold Increase over Control) | 1.00 ± 0.06 | 17.5 ± 0.60** | 1.05 ± 0.02 | 11.48 ± 0.24** |
| Uterine Peroxidase Assay (Abs/uterus) (Fold Increase over Control) | 1.00 ± 0.06 | 28.41 ± 0.73** | 1.56 ± 0.03 | 22.06 ± 0.46** |
| Uterine Peroxidase Assay (Abs/g uterus) Fold Increase over Control) | 1.00 ± 0.06 | 17.7 ± 0.45** | 1.14 ± 0.02 | 14.84 ± 0.31** |
| Uterine cytosolic PR levels (fmol/mg protein) | 308 ± 142 | 674 ± 52* | 338 ± 31 | 677 ± 108* |
| Uterine cytosolic PR levels (fmol/uterus) | 1100 ± 508 | 4501 ± 350* | 1925 ± 177 | 3685 ± 122* |
| Uterine cytosolic PR levels (fmol/g uterus) | 8368 ± 3868 | 21301 ± 1655* | 10693 ± 986 | 18863 ± 625* |

*Significantly different ($p < 0.05$) from control.
**Significantly different ($p < 0.05$) from control.

EXAMPLE 5

Example 5 shows the effect on body and organ weight of treatment with tamoxifen, MCDF, and co-treatment.-

Methods: The procedure for preparing the dosing solutions is as follows: MCDF requires gentle heating to dissolve, and tamoxifen requires that it be dissolved in ethanol (5% of final volume) which is then added to corn oil. The ethanol is evaporated off with a gentle stream of air. First, the corn oil for the tamoxifen dose was heated in a boiling water bath, and allowed to cool. Then, MCDF for both MCDF alone and TAM±MCDF was weighed and dissolved in appropriate amounts of corn oil with heating. For the control vehicle and the MCDF vehicle ethanol was added (5% v/v) and then evaporated away. Tamoxifen for both the tamoxifen treatment and the TAM±MCDF was dissolved in ethanol. An aliquot from each was then added to the appropriate corn oil vehicle (the preheated corn oil for tamoxifen, and the corn oil containing MCDF for TAM+MCDF), and the ethanol was evaporated away.

TABLE 5

Effect of Treatment on Body and Organ Weights

|  | Control | Tamoxifen | MCDF | TAM + MCDF |
| --- | --- | --- | --- | --- |
| Rat weight at start of treatments (g) | 273.1 ± 8.1 | 275.7 ± 7.6 | 274.7 ± 7.0 | 278.3 ± 7.1 |
| Rat weight prior to euthanasia (g) | 293.2 ± 10.9 | 249.8 ± 7.6* | 298.3 ± 5.0 | 250.0 ± 4.5* |
| Spleen wet weight (% body wt) | 0.247 ± 0.007 | 0.252 ± .008 | 0.298 ± 0.015* | 0.253 ± 0.005 |
| Spleen wet weight (g) | 0.720 ± 0.012 | 0.631 ± 0.037 | 0.887 ± 0.043* | 0.632 ± 0.011 |
| Liver weight (% body wt) | 4.06 ± 0.23 | 4.26 ± 0.26 | 4.37 ± 0.26 | 4.03 ± 0.09 |
| Liver weight (g) | 11.88 ± 0.78 | 10.70 ± 0.92 | 13.04 ± 0.87 | 10.06 ± 0.24 |
| Heart weight (% body wt) | 0.319 ± 0.006 | 0.346 ± 0.005 | 0.344 ± 0.014 | 0.354 ± 0.012 |
| Heart weight (g) | 0.935 ± 0.039 | 0.864 ± 0.031 | 1.024 ± 0.037 | 0.863 ± 0.013 |
| kidney weight (% body wt) | 0.318 ± 0.010 | 0.334 ± 0.008 | 0.332 ± .004 | 0.323 ± 0.005 |
| Kidney weight (g) | 0.933 ± 0.038 | 0.837 ± 0.045 | 0.991 ± 0.026 | 0.807 ± 0.016 |

EXAMPLE 6

Example 6 (Tables 6 and 7 and FIGS. 2 and 3) show uterine effects of daily doses of tamoxifen and 6-MCDF in ovariectomized rats.

Figure 2A:
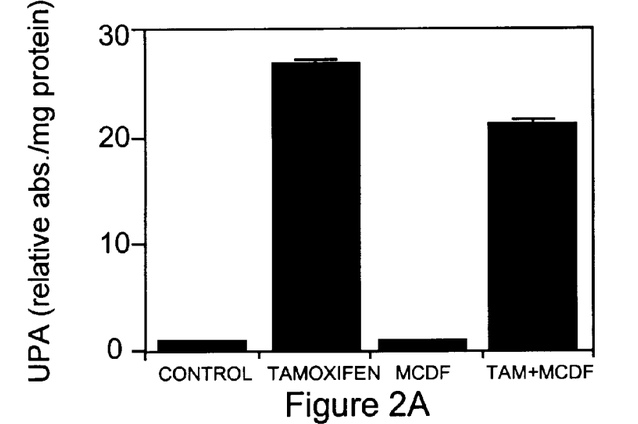
FIGS. 2A, 2B and 2C show uterine peroxidase activity with treatment with tamoxifen, MCDF and co-treatment.
Figure 2B:
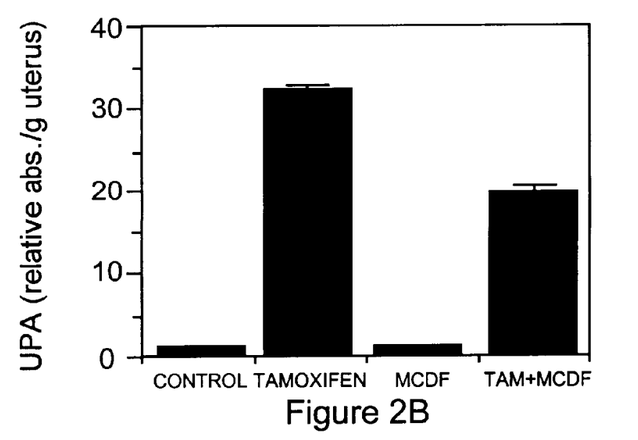
Figure 2C:
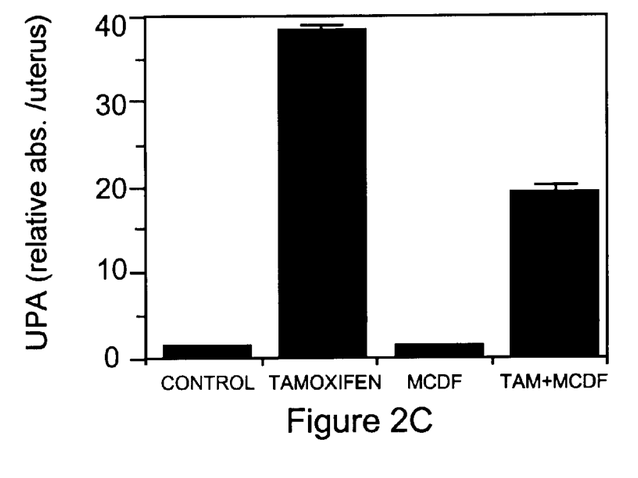

For Table 6 and FIG. 2, rats were ovariectomized at 97 days of age. After approximately 3 weeks, rats were orally dosed for 20 days with corn oil (vehicle), 0.4 mg/kg/day tamoxifen, 0.8 mg/kg/day 6-MCDF, or a cotreatment of 0.4 mg/kg tamoxifen plus 0.8 mg/kg 6-MCDF daily. Rats were euthanized on day 21.

TABLE 6

UTERINE EFFECTS OF DAILY DOSES OF
TAMOXIFEN (0.4 mg/kg) AND 6-MCDF (0.8 mg/kg)
IN THE OVARIECTOMIZED SPRAGUE-DAWLEY RAT
EFFECTS OF TREATMENT ON UTERINE ASSAYS

| ASSAY | CONTROL | TAMOXIFEN | 6-MCDF | TAM + MCDF |
| --- | --- | --- | --- | --- |
| #rats/treatment group | 4 | 5 | 5 | 6 |
| Uterine wet weight (g) | 0.171 ± 0.15 | 0.208 ± 0.009* | 0.131 ± 0.004*† | 0.197 ± 0.009 |
| Uterine wet weight (% body weight) | 0.0583 ± 0.0055 | 0.0857 ± 0.0036* | 0.0454 ± 0.018 ±† | 0.0848 ± 0.0062* |
| Uterine Peroxidase Activity (Absorbance/mg protein)(Fold Increase over control) | 1.00 ± 0.01 | 26.76 ± 0.22* | 0.99 ± 0.01† | 20.87 ± 0.36* |
| Uterine Peroxidase Activity (Absorbance/uterus) (Fold Increase over control) | 1.00 ± 0.01 | 38.66 ± 0.32* | 0.57 ± 0.01*† | 19.55 ± 0.33*† |
| Uterine Peroxidase Activity (Absorbance/g uterus) (Fold Increase over control) | 1.00 ± 0.01 | 31.94 ± 0.26* | 0.88 ± 0.01* | 19.69 ± 0.34*† |

TABLE 6-continued

UTERINE EFFECTS OF DAILY DOSES OF
TAMOXIFEN (0.4 mg/kg) AND 6-MCDF (0.8 mg/kg)
IN THE OVARIECTOMIZED SPRAGUE-DAWLEY RAT
EFFECTS OF TREATMENT ON UTERINE ASSAYS

| ASSAY | CONTROL | TAMOXIFEN | 6-MCDF | TAM + MCDF |
|---|---|---|---|---|
| Uterine Progesterone Receptor (fmol/mg protein) | 198 ± 15 | 790 ± 21* | 152.9 ± 35† | 375 ± 61*† |
| Uterine Progesterone Receptor (fmol/uterus) | 765 ± 69 | 9062 ± 244* | 441.5 ± 100† | 1875 ± 306*† |
| Uterine Progesterone Receptor (fmol/g uterus) | 4462 ± 343 | 43666 ± 1175* | 3985 ± 907† | 11403 ± 1852*† |

Values expressed as means ± standard deviations.
+ Significantly different (p < 0.05) from control treatment.
†Significantly different (p < 0.05) from tamoxifen treatment.

FIGS. 2A, 2B and 2C show uterine peroxidase activity (nuclear extracts) with treatment with tamoxifen, MCDF and co-treatment.

Figure 3A:
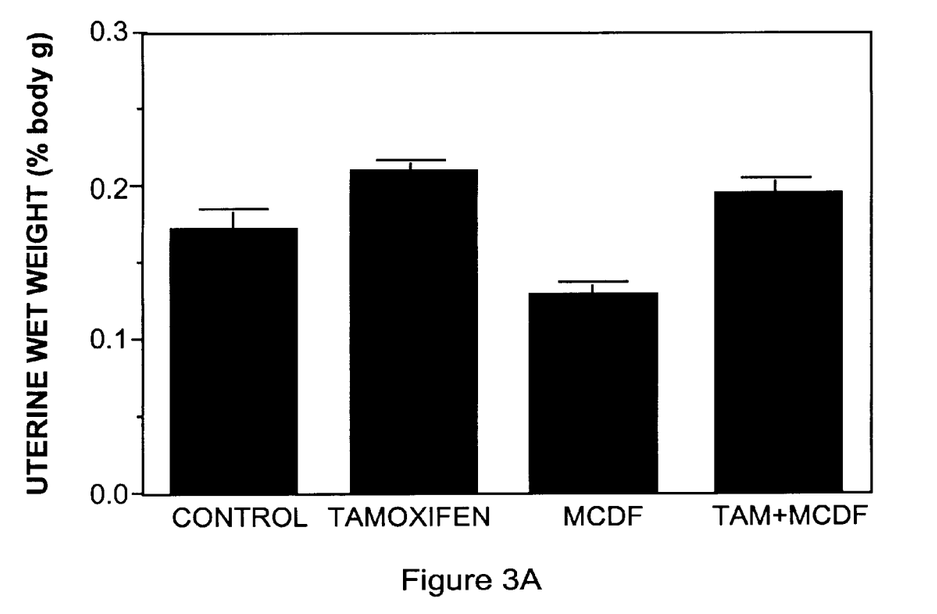
FIGS. 3A and 3B show uterine weights with treatment with tamoxifen, MCDF and co-treatment.
Figure 3B:
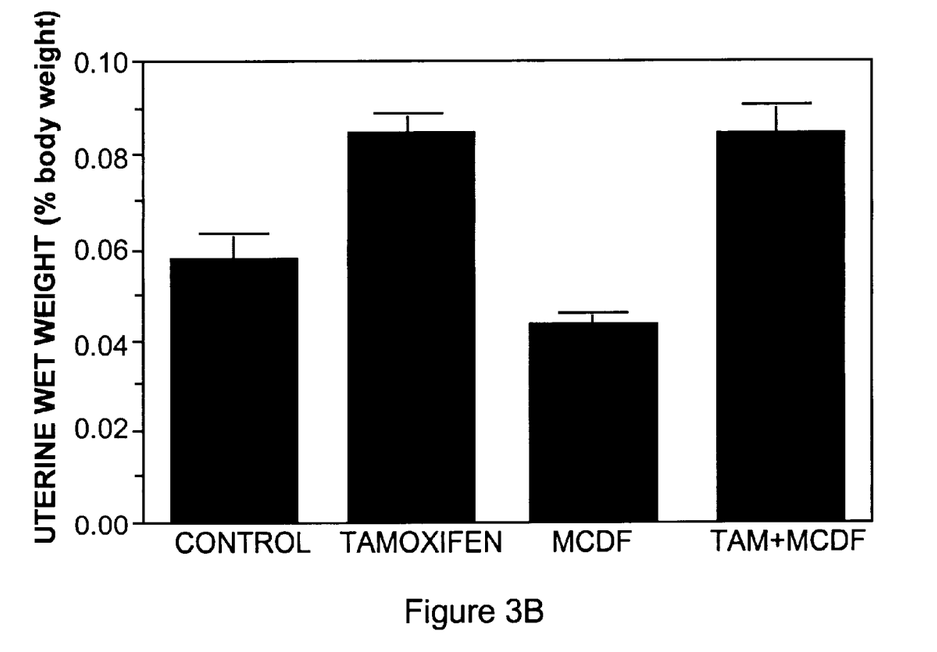

For Table 7 and FIGS. 3 and 3B, exact aged virgin female Sprague-Dawley rats were dosed on day 55 in the afternoon with 20 mg/rat 7,12-dimethylbenz[a]anthacene in a volume of 0.5 ml/rat corn oil (rats weigh approximately 165 g, resulting in 120 mg/kg DMBA and 3 ml/kg corn oil). Rats were treated by gavage daily with corn oil (vehicle), 0.4 mg/kg 6-MCDF, 0.4 mg/kg Tamoxifen, or a cotreatment of 0.4 mg/kg 6-MCDF plus 0.4 mg/kg Tamoxifen for 20 days, and then euthanized on the $21^{st}$ day.

TABLE 7

EFFECTS OF TREATMENT ON BODY AND ORGAN WEIGHTS

| | CONTROL | TAMOXIFEN | 6-MCDF | TAM ± MCDF |
|---|---|---|---|---|
| Rat weight at start of treatments (g) | 255 ± 3 | 261 ± 9 | 257 ± 4 | 244 ± 16 |
| Rat weight prior to euthanasia (g) | 295 ± 11 | 242 ± 6* | 289 ± 7† | 236 ± 11* |
| liver weight (% body weight) | 3.95 ± 0.16 | 4.03 ± 0.15 | 3.78 ± 0.11 | 4.07 ± 0.20 |
| Heart weight (% body weight) | 0.360 ± 0.010 | 0.357 ± 0.023 | 0.356 ± 0.012 | 0.374 ± 0.23 |
| Spleen weight (% body weight) | 0.289 ± 0.018 | 0.254 ± 0.018 | 0.265 ± 0.014 | 0.250 ± 0.004 |
| Kidney weight (% body weight) | 0.334 ± 0.010 | 0.369 ± 0.017 | 0.352 ± 0.015 | 0.357 ± 0.013 |

Values expressed as means ± standard error.
*Significantly different (p < 0.05) from control treatment.
†Significantly different (p < 0.05) from tamoxifen treatment.

FIGS. 3A and 3B show uterine weights with treatment with tamoxifen, MCDF and co-treatment.

REFERENCES

1. B. Astroff et al., 6-Methyl-1,3,8-trichlorodibenzofuran as a 2,3,7,8-tetrachlorodibenzo-p-dioxin antagonist inhibition of the induction of rat cytochrome P-450 isozymes and related monoxygenase activites, *Mol. Pharmacol.* 33 (1988) 231–236;
2. B. Astroff et al., Comparative antiestrongenic activities of 2,3,7,8-tetrachlorodibenzo-p-dioxin and 6-methyl-1,3,8-trichlorodibenozofuran in the female rat, *Itoxicol. Appl. Pharmacol.* 95 (1988) 435–443;
3. B. Astroff et al., 6-Substituted-1,3,8-trichlorodibenzofurans as 2,3,7,8-tetrachlorodibenzo-p-dioxin antagonists in the rat: structure-activity relationships, *Toxicology*, 59 (1989) 285–296;
4. B. Astroff et al., 6-Alkyl-1,3,8-trichlorodibenzofurans as antiestrogens in female Sprague-Dawley rats, *Toxicology* 69 (1991) 187–197;
5. R. Bannister et al., 6-Methyl-1,3,8-trichlorodibenzofuran (MCDF) as a 2,3,7,8-tetrachlorodibenzo-p-dioxin antagonist in C57BL/6 mice, *Toxicology* 54 (1989) 139–150;
6. R. Dickerson et al., Alkyl polychlorinated dibenzofurans and related compounds as antiestrogens in the female rat uterus; structure-activity studies, *Toxicol. Appl. Pharnacol.* 135 (1995) 287–298;
7. G. L. Evans et al., Raloxifene inhibits bone turnover and prevents further cancellous bone loss in adult ovariectomized rats with established osteropenia, *Endo.* (1996) 137:4139–4144;
8. I. Ezawa et al., The effect of ovariectomy on bone metabolism in rats, *Bone* 17:163S-167S;
9. Fisher et al., *J. Natl. Cancer Inst.* (1994); (86):527–537;
10. Fornander et al., *Lancet* (1989); (1):117–120;
11. M. Harris et al., Partial antagonism of 2,3,7,8-tetrachlorodibenzo-p-dioxin-mediated induction of aryl hydrocarbon hydroxylase by 6-methyl-1,3,8-trichlorodibenzofuran; mechanistic studies, *Mol. Pharmacol.* 35 (1989) 729–735;
12. A. McDougal et al., Inhibition of 7,12-dimethylbenz[a]anthracene-induced rat mammary tumor growth by aryl hydrocarbon receptor agonists, *Cancer Letters* (1997) 120:53–63;
13. Mouridsen et al., *Acta. Oncol.* (1998); (27):699–705;
14. Ribeiro et al., *J. Natl. Cancer Inst. Monogr.* (1992); (11):121–125;
15. Rutqvist et al., *J. Natl. Cancer Inst.* (1995); (87):645–651;
16. Ryden et al., *Controlled Clin. Trials* (1986); (7):290–305;
17. Stewart et al., *Lancet* (1989); (1):375–376;
18. Stewart, *J. Natl. Cancer Inst. Monogr.* (1992); (11):117–120;
19. Takahashi et al., The effect of tamoxifen on bone metabolism and skeletal growth is different in ovariectomized and intact rats, *Calcif Tissue Int.* 59:271–276;
20. R. T. Turner et al., Tamoxifen prevents the skeletal effects of ovarian hormone deficiency in rats, *J. Bone and Min. Res.* 2:449–456;
21. C. Yao et al., 2,3,7,8-Tetrachlorodibenzo-p-dioxin-induced porphyria in genetically inbred mice; partial antagonism and mechanistic studies, *Toxicol. Appl. Pharmacol.* 100 (1989) 208–216);

What is claimed is:

1. A method of inhibiting the growth of estrogen-dependent tumors comprising administering to a patient in need of such treatment an enhanced therapeutically effective amount of a first compound of the formula:

wherein $R_1$, $R_3$, $R_6$ and $R_8$ or $R_2$, $R_4$, $R_6$ and $R_8$ are individually and independently a hydrogen or a substituent selected from the group consisting of chlorine, fluorine, and bromine, and a linear or branched alkyl group of one to four carbons, said first compound having at least one alkyl substituent and at least two halogen substituents; and
  a therapeutically effective amount of a second compound which is a triphenylethylene antiestrogen which is tamoxifen.

2. The method of claim 1, wherein the halogen of the first compound is chlorine.

3. The method of claim 1, wherein said halogen substituents of the first compound are selected from the group consisting of chlorine, bromine, and fluorine.

4. The method of claim 1, wherein said alkyl substituents of the first compound are selected from the group consisting of methyl, ethyl and propyl.

5. The method of claim 1, wherein the first compound is 6-methyl-1,3,8-trichlorodibenzofuran.

6. The method of claim 1, wherein the first compound is 8-methyl-1,3,6-trichlorodibenzofuran.

7. The method of claim 1, wherein the first compound is 6-i-propyl-1,3,8-trichlorodibenzofuran.

8. The method of claim 1, wherein the first compound is selected from the group consisting of
  6-methyl-1,3,8-trichlorodibenzofuran,
  8-methyl-1,3,6-trichlorodibenzofuran,
  6-ethyl-1,3,8-trichlorodibenzofuran,
  6-propyl-1,3-8-trichlorodibenzofuran,
  6-methyl-2,3,8-trichlorodibenzofuran,
  6-methyl-2,3,4,8-tetrachlorodibenzofuran,
  8-methyl-1,3,7-trichlorodibenzofuran,
  8-methyl-1,2,4,7-tetrachlorodibenzofuran,
  8-methyl-2,3,7-trichlorodibenzofuran, and
  8-methyl-2,3,7-tetrachlorodibenzofuran.

9. A pharmaceutical combination for inhibiting the growth of estrogen-dependent tumors comprising an enhanced therapeutically effective amount of a first compound of the formula:

or wherein $R_1$, $R_3$, $R_6$ and $R_8$ or $R_2$, $R_4$, $R_6$ and $R_8$ are individually and independently a hydrogen or a substituent selected from the group consisting of chlorine, fluorine, and bromine, and a linear or branched alkyl group of one to four carbons, said first compound having at least one alkyl substituent and at least two halogen substituents; and
  a therapeutically effective amount of a second compound which is a triphenylethylene antiestrogen which is tamoxifen.

10. The pharmaceutical combination of claim 9, wherein the halogen of the first compound is chlorine.

11. The pharmaceutical combination of claim 9, wherein said halogen substituents of the first compound are selected from the group consisting of chlorine, bromine, and fluorine.

12. The pharmaceutical combination of claim 9, wherein said alkyl substituents of the first compound are selected from the group consisting of methyl, ethyl, and propyl.

13. The pharmaceutical combination of claim 9, wherein the first compound is 6-methyl-1,3,8-trichlorodibenzofuran.

14. The pharmaceutical combination of claim 13, wherein the amount of the first compound is about a range of 1 to 50 parts by weight and the second compound is about a range of 1 to 50 parts by weight.

15. The pharmaceutical combination of claim 13, wherein the amount of the first compound is about a range of 1 to 10 parts by weight and the second compound is about a range of 1 to 10 parts by weight.

16. The pharmaceutical combination of claim 13, wherein the amount of the first compound is about a range of 1 to 5 parts by weight and the second compound is about a range of 1 to 5 parts by weight.

17. The pharmaceutical combination of claim 9, wherein the first compound is 8-methyl-1,3,6-trichlorodibenzofuran.

18. The pharmaceutical combination of claim 9, wherein the first compound is 6-i-propyl-1,3,8-trichlorodibenzofuran.

19. The pharmaceutical combination of claim 9, wherein the first compound is selected from the group consisting of
6-methyl-1,3,8-trichlorodibenzofuran,
8-methyl-1,3,6-trichlorodibenzofuran,
6-ethyl-1,3,8-trichlorodibenzofuran,
6-propyl-1,3-8-trichlorodibenzofuran,
6-methyl-2,3,8-trichlorodibenzofuran,
6-methyl-2,3,4,8-tetrachlorodibenzofuran,
8-methyl-1,3,7-trichlorodibenzofuran,
8-methyl-1,2,4,7-tetrachlorodibenzofuran,
8-methyl-2,3,7-trichlorodibenzofuran, and
8-methyl-2,3,7-tetrachlorodibenzofuran.

* * * * *